United States Patent [19]

Engler et al.

[11] Patent Number: 4,753,248
[45] Date of Patent: Jun. 28, 1988

[54] PROBE TRANSLATION SYSTEM FOR USE IN HYPERTHERMIA TREATMENT

[75] Inventors: Mark J. Engler, Durham; James R. Oleson, Chapel Hill; Mark W. Dewhirst, Durham, all of N.C.

[73] Assignee: Duke University, Durham, N.C.

[21] Appl. No.: 66,047

[22] Filed: Jun. 24, 1987

[51] Int. Cl.$^4$ ................................................ A61B 5/00
[52] U.S. Cl. ........................................ 128/736; 128/804
[58] Field of Search .................... 128/804, 736, 303.1; 219/10.55 R, 10.55 A, 10.55 C

[56] References Cited

U.S. PATENT DOCUMENTS

| | | |
|---|---|---|
| 3,306,282 | 2/1967 | Pierce . |
| 3,401,551 | 9/1968 | Maley . |
| 3,531,642 | 9/1970 | Barnes et al. . |
| 3,635,087 | 1/1972 | Conklin . |
| 3,970,074 | 7/1976 | Mogos et al. . |
| 4,186,748 | 2/1980 | Schlager . |
| 4,310,003 | 1/1982 | Schlager . |
| 4,379,461 | 4/1983 | Nilsson et al. . |
| 4,397,314 | 8/1983 | Vaguine . |
| 4,445,516 | 5/1984 | Wollnik et al. . |
| 4,446,874 | 5/1984 | Vaguine ............................ 128/804 |
| 4,531,524 | 7/1985 | Mioduski ........................ 128/804 X |
| 4,557,272 | 12/1985 | Carr ................................... 128/736 |
| 4,586,516 | 5/1986 | Turner . |
| 4,588,307 | 5/1986 | Palti .............................. 128/736 X |
| 4,595,300 | 6/1986 | Kaufman . |

OTHER PUBLICATIONS

"Thermal Mapping In Experimental Cancer Treatment with Hyperthermia: Descriptions and Use of an Automated System" by Gibbs, Jr. in *International Journal of Radiation Oncology Biology Physics*, vol. 9, pp. 1057–1064 (Jul. 1983).

Primary Examiner—Edward M. Coven
Assistant Examiner—Angela D. Sykes
Attorney, Agent, or Firm—Richard E. Jenkins

[57] ABSTRACT

An automated temperature scanning system for monitoring hyperthermia treatment has a linear drive assembly operatively connected to a non-rotational extended-length screw shaft which is linearly translated by a stepper motor. A first tube having a thermometric probe concentrically positioned therein is fixedly secured to the linear drive assembly so as to be motivated thereby. A second tube is secured at one end to an interstitial catheter and is adapted to be at least partially slidably received within the first tube so that linear movement of the first tube toward the second tube slidably moves the thermometric probe within the second tube and an interstitial catheter associated therewith. A computer is electrically connected to the stepper motor to control the movement of the thermometric probe utilizing real time data generated thereby.

23 Claims, 5 Drawing Sheets

PROBE TRANSLATION SYSTEM FOR USE IN HYPERTHERMIA TREATMENT

TECHNICAL FIELD

This invention relates generally to a system for controlling and optimizing the heating pattern used by a hyperthermia device to treat tumors, and more specifically to an automated system of improved design providing for greater accuracy and ease of use so as to enhance the effect of hyperthermia treatment on a patient.

BACKGROUND ART

Hyperthermia treatment provides for the heating of living tissue for therapeutic purposes, most typically the treatment of malignant tumors. Hyperthermia has been used as a method of treating cancer by raising the temperature of a malignant tumor locally since it has been proven that relatively high heat can contribute to the natural regression and/or remission of tumors Hyperthermia treatment can be used as an independent therapy or it may be used in conjunction with other cancer therapies such as radiation, surgery, chemotherapy, and immunotherapy to enhance the effectiveness of the other therapeutic treatments.

Typically, in hyperthermia treatment a tumor is heated to a temperature slightly below that which would injure normal cells in order to thermally destroy it. The treatment is believed to be effective because many types of malignant cell masses have been found to have less heat dissipation capability than normal tissues do, due apparently, to reduced blood flow characteristics. The most common types of hyperthermia modality used presently are radiofrequency, microwave and ultrasound treatment. Radiofrequency and microwave equipment can be used for local, regional and whole body heating. Ultrasound can be used for local and regional heating.

Hyperthermia is presently in an early stage of dose quantification which is similar to that of conventional ionizing radiotherapy of the early twentieth century. Development of dosimetric indices with therapeutic significance strongly depends on the few temperature measurements which are made interstitially. However, problems of scanning thermometers in tissues include choices of measurement dwell times and inter-measurement spacing. With present hyperthermia heat delivery systems, manual scanning of thermometric probes within tissues is awkward. Also, slippage of thermometry catheters and other difficulties limit the extent and accuracy of manual probe temperature scanning. Nevertheless, detailed and strategic temperature measurements are vital to hyperthermia treatment planning. Thus, an improved temperature scanning system for use in hyperthermia treatment is greatly needed at this time.

An automated device presently utilized for thermal mapping is the BSD-1000 manufactured by BSD Medical Corporation of Salt Lake City. This computer controlled apparatus is adapted to move from one to eight thermometric probes within stationary catheters which have been inserted into the tissue volume of interest. The probes are moved at fixed distance intervals through the catheters during conditions approximating thermal stability and are allowed to remain long enough at each position for sufficient thermal equilibration. The temperature is then recorded and the probe withdrawn or moved to the next position. The apparatus utilizes only one stepper motor and therefore the eight thermometric probes are all forced to move within catheters for the same scan length and all utilize the same measurement spacing and dwell time. Moreover, the device utilizes a friction drive and a probe translation mechanism which can result in bending of one or more of the thermometric probes with the resulting problems and inaccuracies which can result therefrom. Because of the relatively large size and rigidity of BSD thermometry tubes, it is difficult to position multiple probes at varying angles to each other and it is not possible to use these tubes for translation of widely used thermometers that are more fragile than BSD thermometers.

Therefore, a need exists for an automated system which will allow for more efficient, accurate and versatile thermal mapping by the movement of thermometric probes within stationary catheters which have been inserted into tissue volume of interest. The new system should overcome the shortcomings presently existing in both manual and automated apparatus now available for use in thermal mapping associated with hyperthermia treatment.

DISCLOSURE OF THE INVENTION

The system of the present invention for characterizing the heating pattern for a hyperthermia device is an improvement over the prior art and overcomes the shortcomings inherent in previous thermal mapping equipment.

The automated temperature scanning system of the present invention is comprised of a stepper motor and an operatively connected linear drive assembly which are mounted at one end of an adjustable support arm which has a magnetic base secured to the other end thereof. The linear drive assembly comprises a plug element which is secured to one end of an extended-length, non-rotating screw shaft extending through the stepper motor and linearly driven by a rotating armature within the motor. A thermometer linear translation assembly is connected to the linear drive assembly and comprises a first tube secured to the plug element of the linear drive assembly. The first tube includes a thermometric probe secured thereto and positioned substantially concentrically therein. The thermometer translation assembly also includes a second tube which is at least partially slidably received by the first tube and is secured at its remote end to an interstitial catheter. In this fashion, linear movement of the first tube toward the second tube causes the thermometric probe to be slidably moved within the second tube and an associated interstitial catheter. Finally, computer means comprising selected hardware and software is electrically connected to the stepper motor in order to control the movement of the thermometric probe within an interstitial catheter.

The stepper motor and linear drive assembly of the present invention allow for very precise control of the linear movement imparted to a thermometric probe, and the telescoping guide described hereinbefore provides for precise support and guidance of a thermometric probe and obviates any tendency to kink or bend and the inaccuracies of measurement which can result therefrom. In this fashion, an improved computer controlled automated temperature scanning system is provided which may be used either singularly or with multiple units connected to a computer. The system provides for independent control and accurate real time data from each automated scanner.

It is therefore the object of this invention to provide an improved temperature scanning system which will provide for greater accuracy and ease of use than temperature scanning systems used in conjunction with hyperthermia systems heretofore.

It is another object of the present invention to provide a temperature scanning system which allows for independent and simultaneous control of each thermometric probe if a plurality of the units are utilized in thermal mapping procedures associated with hyperthermia treatment.

It is still another object of the present invention to provide a temperature scanning system which will not kink or bend a thermometric probe being translated thereby and which can handle more fragile thermometric probes than has heretofore been feasible with an automated system.

DESCRIPTION OF THE DRAWINGS

Some of the objects of the invention having been stated, other objects will become evident as the description proceeds, when taken in connection with the accompanying drawings, in which.

BEST MODE FOR CARRYING OUT THE INVENTION

Figure 1:
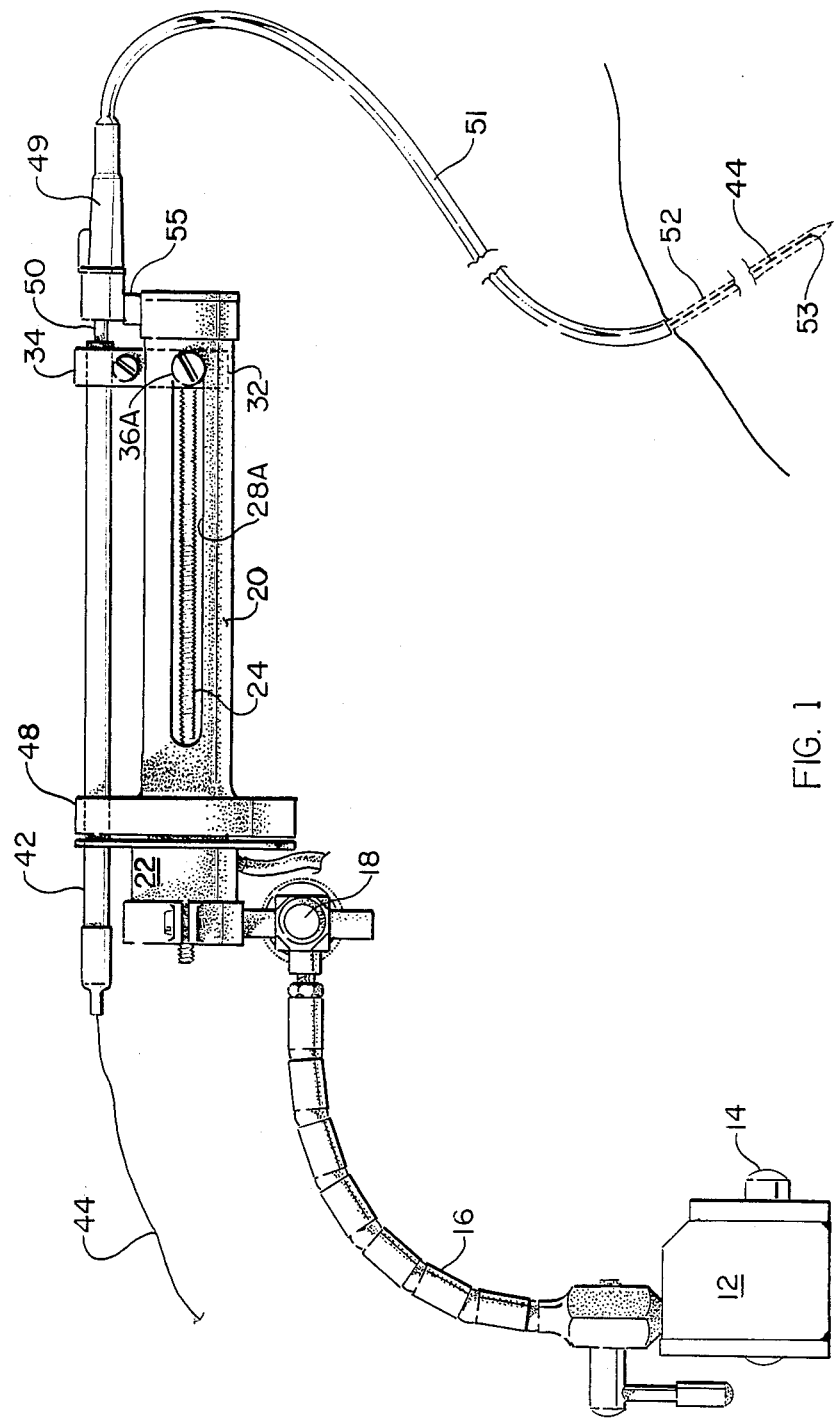
FIG. 1 is a side elevation view of the temperature scanning apparatus of the present invention.
Figure 2:
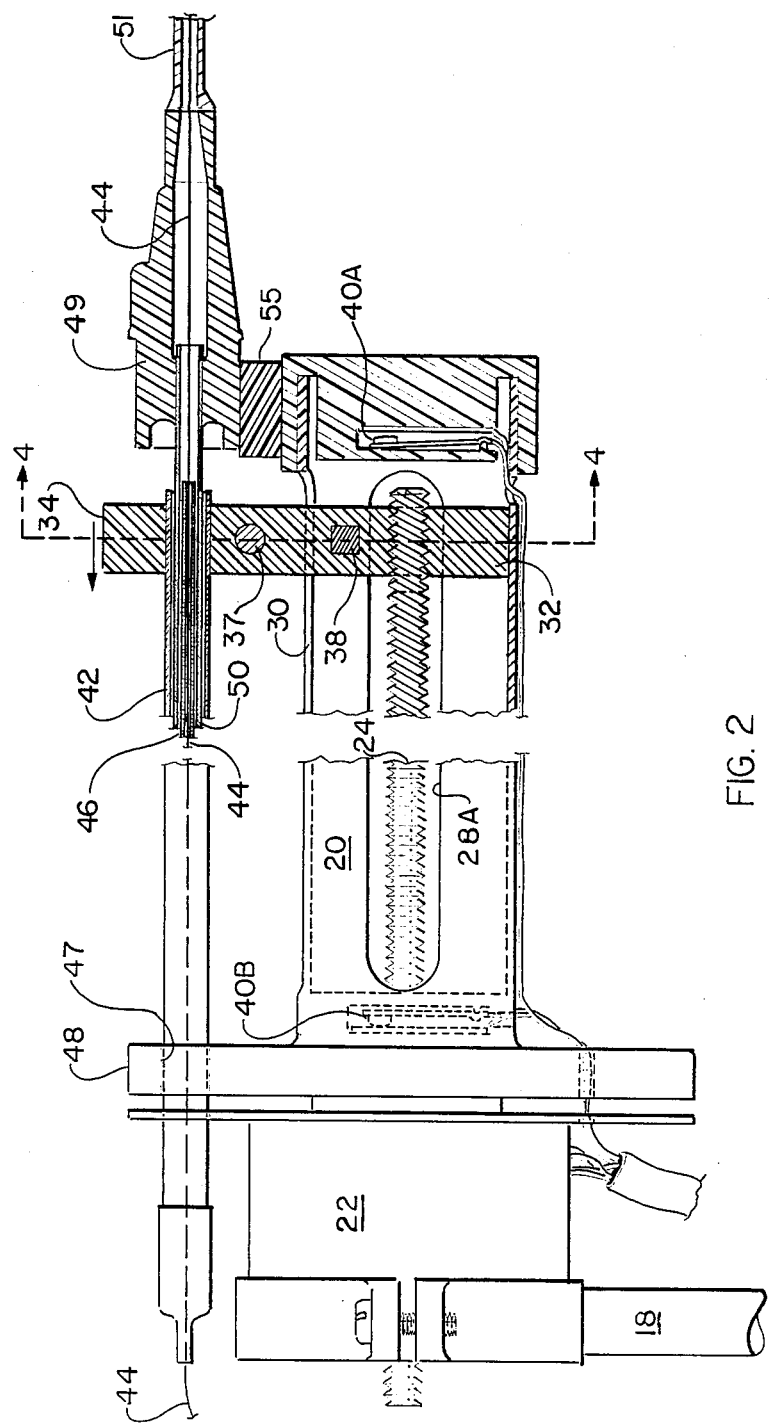
FIG. 2 is a vertical cross-section view of a portion of the apparatus of the present invention before it has been actuated in order to withdraw an associated thermometric probe from the tip of an interstitial catheter.
Figure 3:
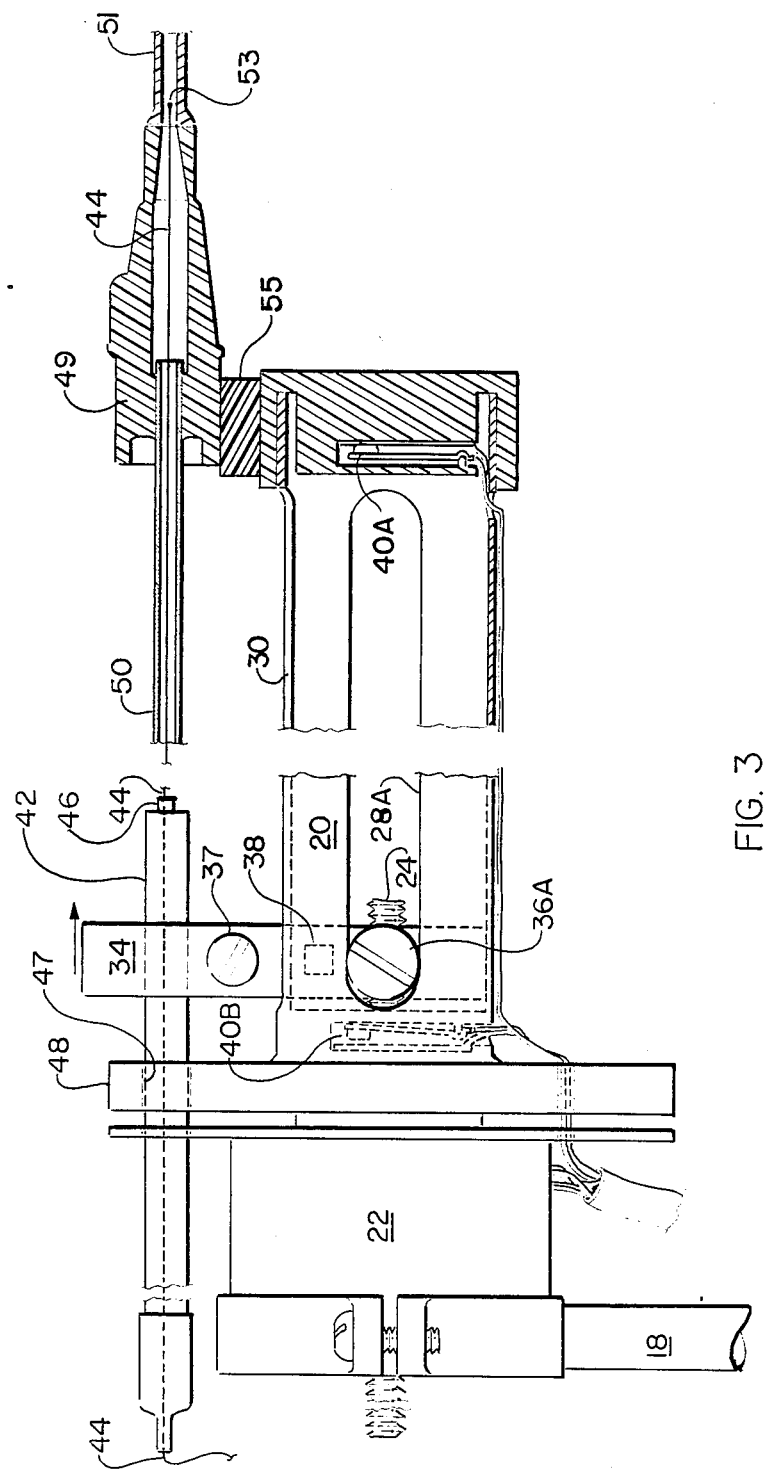
FIG. 3 is a vertical cross-section view of a portion of the apparatus of the present invention after it has been actuated in order to withdraw the associated thermometric probe.
Figure 4:
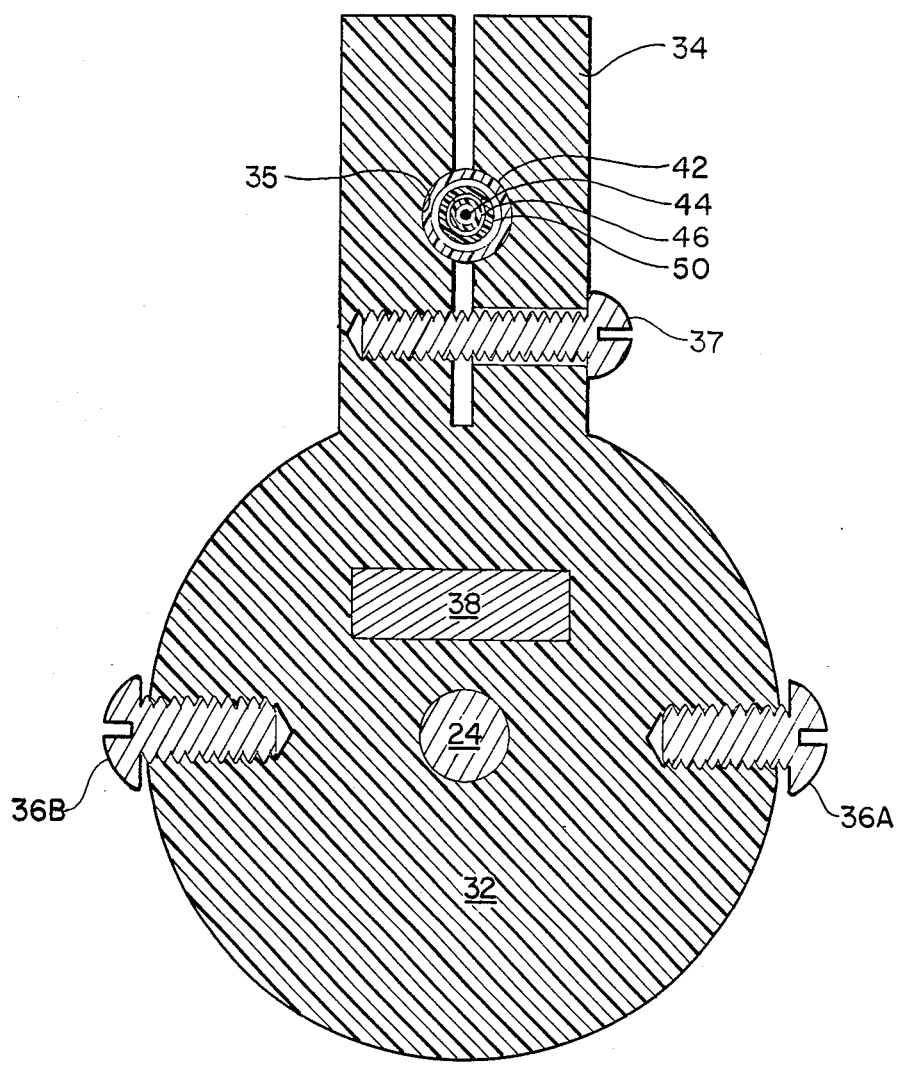
FIG. 4 is a vertical section taken substantially at the line 4—4 of FIG. 2.
Figure 5:
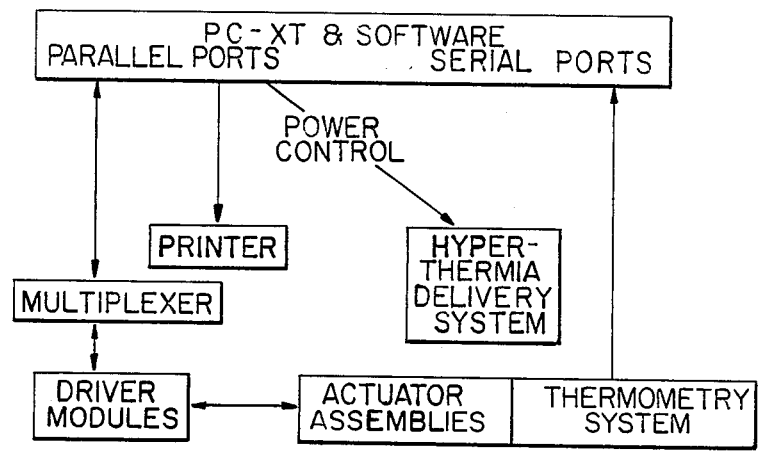
FIG. 5 is a simplified block diagram of the temperature scanning system according to the invention.

Referring now more specifically to the drawings, a preferred embodiment of a temperature scanning system for use in hyperthermia treatment according to the present invention is shown in FIGS. 1–5. The temperature scanning apparatus shown in FIGS. 1–4 comprises a base 12 which may be magnetized as needed by pushing button 14 so that base 12 can be fixed to the metal slats or the like along the side rails of a hyperthermia treatment couch. An adjustable, pivotable support arm 16 is secured at one end to base 12 and at the other end to a mounting means including adjustable mount 18 secured to stepper motor 22. Stepper motor 22 mounted to adjustable mount 18 includes a non-rotational shaft 24 which is driven by an internally rotating armature (not shown) within stepper motor 22. Cylinder 20 is adapted to fit over the collar of stepper motor 22 and includes two longitudinally extending parallel slots 28A, 28B (not shown) positioned on opposite sides of cylinder 20 and a third longitudinally extending and parallel slot 30 which is coextensive with side slots 28A, 28B (not shown) and is located at the top of cylinder 20.

A drive assembly for the temperature scanning apparatus of the present invention includes plug 32 (see FIGS. 2 and 4) fixed to the end of non-rotational shaft 24 and having a shaft plug extension 34 which extends through top slot 30. Shaft plug extension 34 defines a slotted aperture 35 therein which can be adjustably tightened by screw 37 about a thermometer translation assembly to be described in detail hereafter. Plug 32 also includes guide screws 36A, 36B on opposing sides thereof which extend through longitudinally extending slots 28A, 28B, respectively, in order to guide the linear movement of plug 32 within cylinder 20. A magnet 38, is embedded in plug 32 and serves to trip reed switches 40A, 40B mounted at opposing ends of cylinder 20 so as to de-actuate stepper motor 22 when plug 32 reaches the furthermost ends of its travel in order to prevent non-rotational shaft 24 from being driven by stepper motor 22 beyond the mechanical limits of cylinder 20. Although this is matter of design choice, it is anticipated that the preferred embodiment of the invention will allow for travel of plug 32 for a linear distance of between about 2 centimeters and 20 centimeters.

The linear motion provided by stepper motor 22 and non-rotational shaft 24 is translated to a thermometric probe by a thermometer translation assembly. The thermometer translation assembly comprises a first guide or tube 42 (see FIGS. 2 and 3) which is fixedly secured to shaft plug extension 34 and includes a thermometric probe lead 44, most suitably a fiber optic thermometer of the type manufactured by Luxtron Corporation, secured thereto and positioned concentrically therein. First tube 42 most suitably also includes a second tube 46 concentrically positioned therein and of a substantially coextensive length with first tube 42. Second tube 46 surrounds thermometric probe lead 44 so that thermometric probe lead 44, second tube 46 and first tube 42 are all parallel and concentric to each other. First tube 42 slidably extends through an aperture 47 within flange 48 extending around the proximal end of cylinder 20 so that first tube 42 may freely slide therethrough during linear movement thereof by plug 32. A third tube 50 is slidably received within first tube 42 and over second tube 46 so as to be movable in relation thereto. Third tube 50 is connected at its free end to hub 49 connected to flexible connector tube 51 which is in turn connected to fixed interstitial catheter 52 which extends into a tissue volume of interest. Hub 49 is preferably secured to cylinder 20 with a suitable spacer element 55 to assist in maintaining tube 50 colinear with probe lead 44 and deter buckling of tube 50. In this fashion, third tube 50 is fixed relative to first and second tubes 42, 46, respectively, and movement of first tube 42 and second tube 46 by plug 32 serves to move thermometric probe lead 44 and probe 53 within interstitial catheter 52 so as to obtain desired probe position.

Preferably, tubes 42, 46, 50 and flexible connector tube 51 are constructed of plastic, interstitial catheter 52 is a blind-ended catheter suitable for thermometry, and thermometric probe 53 is a single or multiple sensor fiber optic probe. Miniature washers can be inserted into interstitial catheter 52 to change its diameter and to accommodate other size thermometric probes 53.

The use of the telescoping guide tube design described herein solves a mechanical problem wherein the inner diameter of tube 46 must be large enough to allow free movement of flexible thermometer probe lead 44, but not so large that kinking or significant bending of the thermometer probe lead is possible. The wall thickness of tube 46 must also be thin, such that the inner diameter of tube 50 is also small enough to prevent kinking of thermometer probe lead 44 when tube 46 is displaced relative to tube 50, and only tube 50 constrains the thermometer against kinking. This design requires tube 46 itself to have limited resistance to bending and kinking by virtue of its small inner diameter and wall thickness. To compensate for the flexibility of tube 46, tube 42, relatively rigid, has an inner diameter sufficiently small to constrain tube 46 relative to bending and kinking, while still allowing tube 50 to move relative to tube 42. Mechanical strength and rigidity of the thermometer translation assembly is thus accomplished by the configuration of the telescoping tubes.

Finally, the apparatus of the invention includes control means, most suitably computer means, electrically connected to stepper motor 22 for controlling the movement of thermometric probe 53 within interstitial catheter 52. A better understanding of the preferred computer control can be had with reference to FIG. 5 of the drawings. Most suitably, a personal computer with at least 1 Megabyte of RAM and a hard disc with at least 20 Megabytes of memory and less than 30 milliseconds access time is used to control one or more of the temrature scanning apparatus through one or more parallel ports of the computer or one parallel port and an external multiplexer. The computer provides for independent control of each scanning apparatus since each thermometric probe 53 is being linearly translated by a separate stepper motor 22 and thermometer translation assembly. Signals derived from each thermometric probe 53 within its respective interstitial catheter 52 are serial ported back to the memory of the computer. This particular configuration forms a loop allowing for real time temperature feedback control and display of variables such as temperature (T), temperature difference between points ($\Delta T$), position (r), spacing ($\Delta r$), time (t) and dwell time ($\Delta t$). These can be displayed in graphic or tabular form, for example, T as a function of r or t, or $\Delta t$ as a function of r. For hyperthermia treatments scan parameters are ideally functions of the measured temperatures.

Most suitably, each temperature scanning apparatus is connected to the computer in a conventional fashion. Software is utilized which allows T to be analyzed and scan parameters to be altered by keyboard entries or software in an automatic mode. Software is utilized which can independently control up to six temperature scanning apparatus and provide monitor screens with data from multiple channels in real time. All of the software is modular in design with a choice of algorithms for generating scan patterns from cumulative T(r,t), and it is most suitably stored on the hard disk of the computer. Summarily, the hardware serves to interface the computer with the one or more temperature scanning apparatus utilized therewith, and the software serves to regulate thermometric probe movements and to display temperature profiles for each temperature scanning apparatus.

The temperature scanning system of the present invention allows for the use of one or more independently controlled thermometric probes within a tissue volume of interest. The apparatus allows for substantial geometric latitude in the placement of a plurality of interstitial catheters in close proximity to each other as well as more precise translation of thermometric probes within the tissue volume. Moreover, shortcomings of previous systems relating to bending or buckling of probe leads within large diameter guides have been overcome with the telescopic tube thermometer translation assembly utilized in the apparatus of the invention.

Although thermometric probe translation has been described hereinabove it should also be appreciated that the system of the invention can be used to translate probes other than thermometers, for example, radiation detectors, pressure detectors or blood flow meters. Thus the invention can be applied to scan physical characteristics other than temperature. Moreover, it should be further appreciated that the system of the invention can be used to scan materials other than tissues, for example, the containment vessel of a nuclear reactor and the like.

It will thus be understood that various details of the invention may be changed without departing from the scope of the invention. Furthermore, the foregoing description is for the purpose of illustration only, and not for the purpose of limitation—the invention being defined by the claims.

What is claimed is:

1. An automated temperature scanning system for monitoring hyperthermia treatment and the like comprising;
    a base;
    a support having two ends, said support secured at one end to said base;
    means for mounting a motor and drive assembly secured to the other end of said support;
    a motor secured to said mounting means;
    a linear drive assembly operatively connected to said motor;
    a thermometer translation assembly operatively connected to said linear drive assembly and comprising:
        a first tube secured to said linear drive assembly and adapted for linear motivation thereby, said first tube having a thermometric probe secured thereto and positioned substantially concentrically therein;
        a second tube having two ends, one end of said second tube being slidably received and said second tube being at least partially slidably received by said first tube, and said second tube adapted at the other end to be secured to a catheter, so that linear motivation of said first tube toward said second tube causes the thermometric probe to be slidably moved within said second tube and said catheter; and
    control means electrically connected to said motor for controlling the insertion of the thermometric probe into said catheter.

2. An automated temperature scanning system according to claim 1 wherein said base is magnetized.

3. An automated temperature scanning system according to claim 1 wherein said support comprises a plurality of relatively pivotably movable segments.

4. An automated temperature scanning system according to claim 1 wherein said mounting means includes a cylinder supporting said linear drive assembly and said thermometer translation assembly.

5. An automated temperature scanning system according to claim 1 wherein said motor comprises a stepper motor having an extended length non-rotating screw shaft therethrough which is linearly motivated by a rotating armature within said stepper motor.

6. An automated temperature scanning system according to claim 5 wherein said linear drive assembly comprises a plug element secured to one end of said screw shaft extending through said stepper motor, said plug element also being fixedly secured to said first tube so as to effectuate linear movement thereof corresponding to the linear movement of said screw shaft effectuated by said stepper motor.

7. An automated temperature scanning system according to claim 6 wherein said linear drive assembly includes magnetic means carried by said plug element and reed switch means associated with said mounting means and electrically connected to said stepper motor to limit the length of linear movement of said plug element.

8. An automated temperature scanning system according to claim 1 wherein said first tube of said thermometer translation assembly is of greater diameter than said second tube.

9. An automated temperature scanning system according to claim 8 wherein said thermometer translation assembly includes a third tube concentrically positioned within and secured to said first tube so as to surround said thermometric probe therein, said third tube being substantially coextensive with said first tube and slidably received within said second tube.

10. An automated temperature scanning system according to claim 1 wherein said first tube of said thermometric translation assembly is of smaller diameter than said second tube.

11. An automated temperature scanning system according to claim 10 wherein said thermometer translation assembly includes a third tube concentrically positioned within and secured to said second tube so as to surround said thermometric probe therein, said third tube being substantially coextensive with said second tube and adapted to be slidably received within said first tube.

12. An automated temperature scanning system according to claim 1 wherein said control means comprises a computer adapted to give real time feedback control and display of scan parameters comprising temperature (T), temperature difference between points ($\Delta T$), position (r), spacing ($\Delta r$), time (t) and dwell time ($\Delta t$).

13. An automated temperature scanning system for monitoring hyperthermia treatment and the like comprising;
   a base;
   an adjustable support arm having two ends, said support arm secured at one end to said base;
   means for mounting a motor and drive assembly secured to the other end of said support arm;
   a stepper motor having an extended length screw shaft therethrough, said stepper motor being secured to said mounting means;
   a linear drive assembly operatively connected to said motor, said drive assembly including a plug element secured to one end of said screw shaft of said stepper motor and adapted to slidably move along a linear pathway;
   a thermometer translation assembly operatively connected to said linear drive assembly and comprising:
      a first tube secured to said plug element of said linear drive assembly and adapted for linear motivation thereby, said first tube having a thermometric probe secured thereto and substantially concentrically positioned therein;
      a second tube having two ends, one end of said second tube being slidably received and said tube being at least partially slidably received by said first tube, and said second tube adapted at the other end to be secured to a catheter, so that linear motivation of said first tube toward said second tube causes the thermometric probe to be slidably moved within said second tube and said catheter; and
   computer means electrically connected to said motor for controlling the insertion of the thermometric probe into said catheter.

14. An automated temperature scanning system according to claim 13 wherein said base is magnetized.

15. An automated temperature scanning system according to claim 13 wherein said support arm comprises a plurality of relatively pivotably movable segments.

16. An automated temperature scanning system according to claim 13 wherein said mounting means includes a cylinder supporting said linear drive assembly and said thermometer translation assembly and having at least one longitudinally extending guide slot to define the linear pathway of movement of said plug element and said first tube secured thereto.

17. An automated temperature scanning system according to claim 13 wherein said stepper motor comprises a non-rotating screw shaft therethrough which is linearly motivated by a rotating armature within said stepper motor.

18. An automated temperature scanning system according to claim 17 wherein said linear drive assembly further includes magnetic means carried by said plug element and reed switch means associated with said mounting means and electrically connected to said stepper motor to limit the length of linear movement of said plug element.

19. An automated temperature scanning system according to claim 13 wherein said first tube of said thermometer translation assembly is of greater diameter than said second.

20. An automated temperature scanning system according to claim 13 wherein said thermometer translation assembly includes a third tube concentrically positioned within and secured to said first tube so as to surround said thermometric probe therein, said third tube being substantially coextensive with said first tube and slidably received within said second tube.

21. An automated temperature scanning system according to claim 13 wherein said first tube of said thermometric translation assembly is of smaller diameter than said second tube.

22. An automated temperature scanning system according to claim 13 wherein said thermometer translation assembly includes a third tube concentrically positioned within and secured to said second tube so as to surround said thermometric probe therein, said third tube being substantially coextensive with said second tube and slidably received within said first tube.

23. An automated temperature scanning system according to claim 13 wherein said computer means is adapted to give real time feedback control and display of scan parameters comprising temperature (T), temperature difference between points ($\Delta T$), position (r), spacing ($\Delta r$), time (t) and dwell time ($\Delta t$).

* * * * *